(12) United States Patent
Hamilton et al.

(10) Patent No.: US 10,112,156 B2
(45) Date of Patent: Oct. 30, 2018

(54) THERMODYNAMIC SOLUTIONS OF METAL CHALCOGENIDES AND MIXED METAL OXIDES AND CHALCOGENIDES

(75) Inventors: James P. Hamilton, Platteville, WI (US); Lester F. Lampert, Madison, WI (US)

(73) Assignee: WISYS TECHNOLOGY FOUNDATION, INC., Madison, WI (US)

( * ) Notice: Subject to any disclaimer, the term of this patent is extended or adjusted under 35 U.S.C. 154(b) by 1245 days.

(21) Appl. No.: 14/002,916

(22) PCT Filed: Mar. 5, 2012

(86) PCT No.: PCT/US2012/027757
§ 371 (c)(1),
(2), (4) Date: Feb. 11, 2014

(87) PCT Pub. No.: WO2012/119154
PCT Pub. Date: Sep. 7, 2012

(65) Prior Publication Data
US 2014/0147398 A1    May 29, 2014

Related U.S. Application Data

(60) Provisional application No. 61/448,970, filed on Mar. 3, 2011.

(51) Int. Cl.
*H01B 1/24*    (2006.01)
*C08J 3/05*    (2006.01)
(Continued)

(52) U.S. Cl.
CPC .............. *B01F 1/00* (2013.01); *A61K 8/0241* (2013.01); *A61K 8/044* (2013.01); *A61K 8/19* (2013.01);
(Continued)

(58) Field of Classification Search
CPC ......... B01F 1/00; A61K 8/0241; A61K 8/044; A61K 8/19; A61K 8/29; A61Q 17/04;
(Continued)

(56) References Cited

U.S. PATENT DOCUMENTS

| | | |
|---|---|---|
| 2008/0194709 A1 | 8/2008 | Hecaen |
| 2010/0035047 A1 | 2/2010 | Ajayan et al. |

(Continued)

FOREIGN PATENT DOCUMENTS

| | | |
|---|---|---|
| JP | S62-211596 | 9/1987 |
| JP | 62-279838 | 12/1987 |

(Continued)

OTHER PUBLICATIONS

Kathiravan et al., "Effect of anchoring group on the photosensitization of colloidal TI02 nanoparticles with porphyrins", Journal of Colloid and Interface Science 331 (2009) 401-407.

(Continued)

*Primary Examiner* — Harold Y Pyon
*Assistant Examiner* — Danny N Kang
(74) *Attorney, Agent, or Firm* — Boyle Fredrickson, S.C.

(57) ABSTRACT

The present invention includes a solvent system comprising a pristine nanoparticle solute suspended in a liquid solvent. The solute is selected from the group consisting of a metal oxide, a mixed metal oxide, a chalcogenide, and a mixed metal chalcogenide; and the solvent system is characterized by a value of chi less than about 0.00.

2 Claims, 12 Drawing Sheets

(51) Int. Cl.
  H01B 1/22    (2006.01)
  B01F 1/00    (2006.01)
  A61K 8/29    (2006.01)
  A61Q 17/04   (2006.01)
  C01G 23/047  (2006.01)
  H01M 4/04    (2006.01)
  H01M 4/485   (2010.01)
  A61K 8/02    (2006.01)
  A61K 8/04    (2006.01)
  A61K 8/19    (2006.01)
  H01G 11/26   (2013.01)
  H01M 4/48    (2010.01)
  B82Y 30/00   (2011.01)
  H01M 10/0525 (2010.01)
  B82Y 99/00   (2011.01)

(52) U.S. Cl.
  CPC ............ A61K 8/29 (2013.01); A61Q 17/04 (2013.01); B82Y 30/00 (2013.01); C01G 23/047 (2013.01); H01G 11/26 (2013.01); H01M 4/0402 (2013.01); H01M 4/0404 (2013.01); H01M 4/48 (2013.01); H01M 4/485 (2013.01); A61K 2800/413 (2013.01); B82Y 99/00 (2013.01); C01P 2002/82 (2013.01); C01P 2004/03 (2013.01); C01P 2004/16 (2013.01); H01M 10/0525 (2013.01); Y10S 977/832 (2013.01)

(58) Field of Classification Search
  CPC ...... B82Y 30/00; B82Y 99/00; C01G 23/047; H01G 11/26; H01M 4/0404; H01M 4/48; H01M 4/485; H01M 10/0525; H01M 4/0402; C01P 2004/03; C01P 2004/16; C01P 2002/82; Y10S 977/832
  USPC ............................................. 252/500
  See application file for complete search history.

(56) References Cited

U.S. PATENT DOCUMENTS

| | | | |
|---|---|---|---|
| 2010/0143823 A1* | 6/2010 | Tanaka | H01M 8/1016 429/483 |
| 2011/0111299 A1* | 5/2011 | Liu | B82Y 30/00 429/221 |
| 2011/0140580 A1 | 6/2011 | Yang et al. | |

FOREIGN PATENT DOCUMENTS

| | | |
|---|---|---|
| JP | H10-323551 | 12/1998 |
| JP | H11-194042 | 7/1999 |
| JP | 2000-038329 | 2/2000 |
| JP | 2000-080021 | 3/2000 |
| JP | 2000-334286 | 12/2000 |
| JP | 2002-234995 | 8/2002 |
| JP | 2002-542311 | 12/2002 |
| JP | 2006-093002 | 4/2006 |
| JP | 2006-093037 | 4/2006 |
| JP | 2006-210135 | 8/2006 |
| JP | 2006-301615 | 11/2006 |
| JP | 2006-306793 | 11/2006 |
| JP | 20178-001578 | 1/2008 |
| JP | 2008-520794 | 6/2008 |
| JP | 2008-537704 | 9/2008 |
| JP | 2009-090272 | 4/2009 |
| JP | 2009-524567 | 7/2009 |
| JP | 2010-501710 | 1/2010 |
| JP | 2010-114086 | 5/2010 |
| JP | 2010-138020 | 6/2010 |
| JP | 2010-225487 | 10/2010 |
| JP | 2012-176331 | 9/2012 |
| JP | 2013-198851 | 10/2013 |
| WO | 2005006482 | 1/2005 |
| WO | 2010027336 | 3/2010 |

OTHER PUBLICATIONS

Pastoriza-Santos et al., "N,N-Dimethylformamide as a Reaction Medium for Metal Nanoparticle Synthesis", Advanced Functional Materials, 2009, 19, 679-688.

Estruga et al., "Low temperature N,N-dimethylformamide-assisted synthesis and characterization of anatase-rutile biphasic nanostructured titania", Nanotechnology 20 (2009) 125604, 7 pages.

Jan U. Wineke et al: "Systematic Investigation of Dispersions of Unmodified Inorganic Nanoparticles in Organic solvents", Ind. Eng. Chem.Res, vol. 51, No. 1, Dec. 12, 2011 (Dec. 12, 2011), pages.

M. Estruga et al: "Low temperature N,N-demethylformamide-assisted synthesis and characterization of anatase rutile biphasic nanostructured titania", Nanotechnology, vol. 20, No. 12, 125604.

A. Kathiravan: Effect of Anchoring group on the Photosensitization of Colloid Ti02 nanoparticules with porphyrins, Journal of Colloid and Interface Science, vol. 331, Dec. 3, 2008 (Dec. 3, 2008).

Isabel Pastoriza-Santos: "N,N-Dimethylformamide as a Reaction Medium for Metal Nanoparticle Synthesis", Advanced Functional Materials, vol. 19, No. 5, Mar. 10, 2009 (Mar. 10, 2009).

Japanese Patent Appln. No. 2013-556679, Office Action dated Sep. 6, 2016, 5 pages.

Japanese Patent Appln. No. 2013-556679, Office Action dated Feb. 7, 2017, 8 pages.

* cited by examiner

THERMODYNAMIC SOLUTIONS OF METAL CHALCOGENIDES AND MIXED METAL OXIDES AND CHALCOGENIDES

CROSS REFERENCE TO RELATED APPLICATION

This application claims the benefit of U.S. Provisional Patent Application Ser. No. 61/448,970 entitled "Thermodynamic solutions of metal oxides and metal chalcogenides and mixed metal oxides and chalcogenides" filed Mar. 3, 2012 hereby incorporated by reference herein in its entirety.

STATEMENT REGARDING FEDERALLY SPONSORED RESEARCH OR DEVELOPMENT

Field of the Invention

The present invention relates to solvents for macromolecule and nanoparticle solutes, including, for example, solutes of metal oxides, metal chalcogenides, mixed metal oxides, and mixed metal chalcogenides, as well as methods of using these solvents for the manufacture of articles and materials.

Background of the Invention

There exists significant interest in identifying effective solvents to promote uniform dispersion of metal oxides, metal chalcogenides, mixed metal oxides, and mixed metal chalcogenides that exist either as nanocrystals and lamellar materials. Normally these "sands", powders, macromolecules and nanocrystals are textbook examples of insoluble, undispersible materials and the powders they form, tend to exist as clumps, which in turn diminish the functional capabilities of the macromolecules and nanocrystals. A more uniform dispersion of macromolecules, crystal powders and nanocrystals can improve composite materials, solutions or surface coatings that use those macromolecules.

In the context of oxides and chalcogenides, historically, a process called sputter coating was developed to disperse these materials that do not evaporate easily when heated. In this process, a given oxide or chalcogenide is released from a thin layer target and deposited on a substrate as a result of being bombarded by energized particles. However, this process is unsuitable for many manufacturing processes, for example, the dispersion of these macromolecules within other materials in a matrix form for the application of these macromolecules to thermoplastics and the like which may not accommodate high temperatures. Sputtering is also very expensive and requires high vacuum equipment. The technology described herein is replacement for sputtering and Sol Gel technologies.

SUMMARY OF THE INVENTION

The present inventors have identified solvents for a metal oxides, metal chalcogenides, mixed metal oxides, and mixed metal chalcogenides, including minerals such as clays, previously thought to be insoluble in their pristine state. This discovery has, in turn, lead to the development of a number of thermodynamically stable liquid, solid or gel matrix materials incorporating these macromolecules and processes using these solvents.

Solvent Systems

The present inventors have determined the properties of high-quality solvents for various macromolecules including metal oxides, metal chalcogenides, mixed metal oxides, and mixed metal chalcogenides, permitting nanoparticles of these compounds to be extracted from macromolecules. Example solvents include: DMF, CPO, CHP, NMP, IPA, Xylenes and mixtures thereof.

Solvent-Enabled Products

The discovery of a solvent for metal oxides, metal chalcogenides, mixed metal oxides, and mixed metal chalcogenides has enabled various novel applications, including both processes and products. High efficiency Li-ion battery and ultracapcitor electrodes may be created from a hybrid material of liquid soluble $TiO_2$ or other metal oxide and graphene. Nanowire dispersions may be created from liquid soluble $TiO_2$ nanocrystals and nanowires. A low haze, self cleaning and ultraviolet resistant coating may be created from liquid soluble $TiO_2$.

DETAILED DESCRIPTION OF THE INVENTION

I. Instrument and Method of Use

Figure 1:
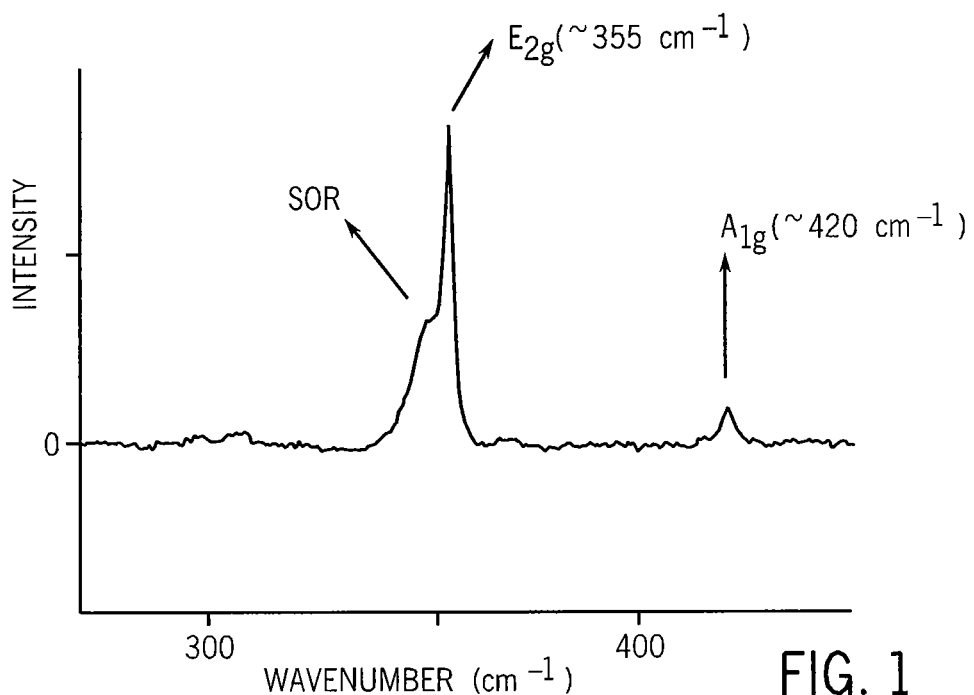
FIG. 1 is an example Raman spectrum showing the $E_{2g}$ and $A_{1g}$ peaks of tungsten disulfide.

The solvent systems of the present invention were identified and characterized using an instrument for solvent quality measurement described in US patent application publication number 2011/0117361 entitled: Method and Apparatus for Identifying and Characterizing Material Solvents and Composited Matrices and Methods of Using Same" filed Jan. 7, 2009 and hereby incorporated by reference in its entirety.

This instrument provided a measure of the solvent system second virial coefficient ($B_2$) according to the following Debye light scattering equation (1):

$$\frac{C_{NT}}{S-S_0} = \frac{B_2}{K'}C_{NT} + \frac{1}{M_w K''} \quad (1)$$

where:

$C_{NT}$ is the concentration of the solute;

S and $S_0$ are dimensionless numbers proportional to the scattering intensity of the solution and pure solvent respectively;

K and K' are instrument constants dependent on the spectrometer characteristics determined by calibration measurements of the spectrometer according to techniques well known in the art;

$B_2$ is the second virial coefficient; and $M_w$ is the molecular weight of the solute.

Once the second virial coefficient is determined ($B_2$), it may be optionally converted to the Flory-Huggins parameter $\chi$ according to the following equation:

$$\chi = \tfrac{1}{2} - B_2 \bar{V}_2 \rho_{NT}^2 \quad (2)$$

where:

$\bar{V}_2$ is the solvent molar volume, and $\rho_{NT}$ is the density of the solute.

Alternatively, the enthalpy of mixing $\Delta H_{Mix}$ may be determined according to the following equation:

$$\frac{\Delta H_{Mix}}{V_{Mix}} = \chi \frac{RT}{V_S}\phi(1-\phi) \quad (3)$$

where:

RT is the gas constant times absolute temperature, and $\phi$ is the solute volume fraction.

Generally, macromolecule solutes such as nanotubes will be thermodynamically soluble when the Gibbs free energy of mixing $\Delta G_{Mix}$ is negative. The Gibbs free energy is described by the following equation (4):

$$\Delta G_M = \Delta H_{Mix} - T\Delta S_{Mix} \quad (4)$$

where:

$\Delta S_{Mix}$ is the entropy of mixing. For solutes with large molecular weight and/or high rigidity there will be an extremely small entropy of mixing $\Delta S_{Mix}$. For this reason thermodynamic solubility requires that $\Delta H_{Mix}$ is small.

Each of these expressions provides an indication of the solvent quality with respect to the particular solute. Note that these three measures of solvent quality $B_2$, $\chi$, and $\Delta H_{Mix}$ have different signs and therefore the best solvent will be indicated by a maximum for $B_2$ and a minimum for $\chi$ and $\Delta H_{Mix}$.

Using this instrument, the inventors determined that the change in the Rayleigh scattering as a function of concentration can accurately reveal the aggregation point of the solution, in particular, when a solute of large molecules such as carbon nanotubes begins to aggregate. This aggregation point can be difficult to determine simply by looking for precipitate.

II Solvent Systems

A. Tungsten Disulfide Nanoparticles

Tungsten disulfide was dissolved in thermodynamic equilibrium (providing a chi value of less than 0) using the solvents of CHP and NMP.

Example 1

Raman spectroscopy was used to characterize the solute of tungsten disulfide using a Raman spectroscopy apparatus including a laser generating a laser light composed of incident photons. The incident photons are absorbed by a rotating sample of nanoparticles formed by the solvent of the present invention and compared to a mechanically exfoliated tungsten disulfide flake using mechanical exfoliation (adhesive tape). A reemitted light comprised of scattered photons exits the sample and passes through a spectrometer prior to being received at a detector. The scattered photons of the reemitted light, i.e., Raman scattering, are photons which exhibit a frequency distinguishable from that of the incident photons, due to phonon interaction within the sample of nanoparticles. Upon receiving the scattered photons, the detector can generate a fingerprint of the molecules comprising the sample.

The fingerprint generated at the detector is produced in the form of a Raman spectrograph comparing the Raman intensity along a y-axis versus a Raman shift along the x-axis. The Raman shift is expressed as wavenumbers in the unit of inverse centimeters ($cm^{-1}$). Peaks in the intensity at specific wavenumbers can be used to identify the molecules comprising the sample.

Referring now to FIG. 1, one illustrative example of a Raman spectrum generated in accordance with this invention is shown. The sample illustrated in the Raman spectrum of FIG. 1 is Tungsten Disulfide ($WS_2$). The $WS_2$ Raman spectrum demonstrates two distinct peaks, one at approximately 355 $cm^{-1}$, corresponding to the $E_{2g}$ vibration mode, and one at approximately 420 $cm^{-1}$, corresponding to the $A_{1g}$ vibration mode.

Figure 2:
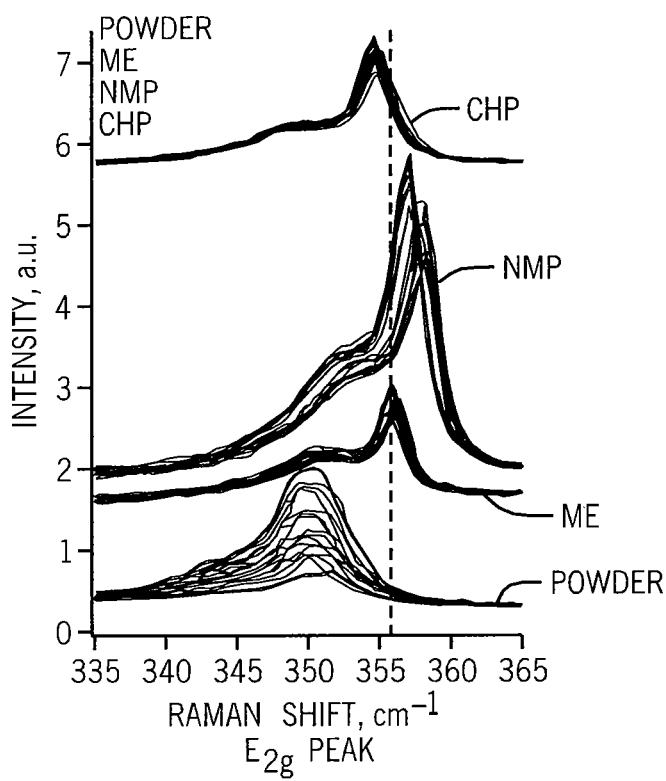
FIG. 2 are Raman spectra of samples of tungsten disulfide prepared with different techniques showing the $E_{2g}$ peak.
Figure 3:
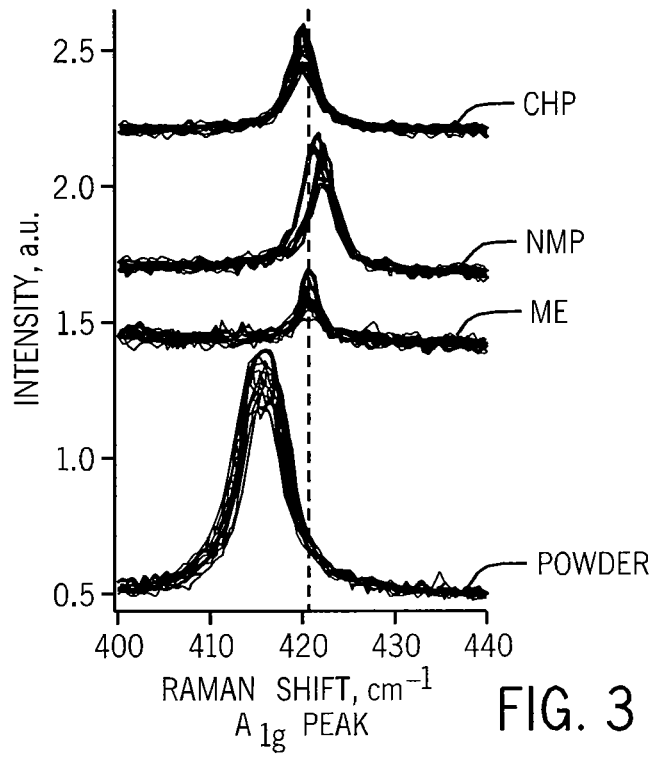
FIG. 3 is a figure similar to that of FIG. 2 showing the $A_{1g}$ peak.

Referring now to FIGS. 2 and 3, two Raman spectra are shown for four distinct samples of $WS_2$, in which the $E_{2g}$ and $A_{1g}$ peaks have been isolated. The four distinct samples of $WS_2$ are distinguished in accordance with their exfoliation technique. The first powdered $WS_2$ sample was exfoliated via previously known mechanical exfoliation (ME), also known as the "scotch tape" method to form flakes from between 2.0 nm to 4.1 nm in height. The second powdered $WS_2$ sample was exfoliated via liquid suspension in an N-methyl-2-pyrrolidone (NMP) solvent. The third powdered $WS_2$ sample was exfoliated via liquid suspension in a 1-cyclohexyl 2-pyrolidine (CHP) solvent. And finally the fourth powdered $WS_2$ sample acted as a control and was not exfoliated. These four samples were then subjected to the Raman spectroscopy procedure discussed above using a 532 nm laser beam and an acquisition time of 5 minutes, while the samples were rotated 360° at approximately 20° increments.

As seen in both FIGS. 2 and 3, the fourth sample, i.e., control sample, demonstrated the lowest intensity and Raman shift at both the $E_{2g}$ and $A_{1g}$ peaks. Alternatively, the third sample which was exfoliated via CHP solvent demonstrated the highest baseline intensity and peak intensity at both the $E_{2g}$ and $A_{1g}$ peaks. The second sample, which was exfoliated via the NMP solvent, demonstrated the highest peak intensity at both the $E_{2g}$ and $A_{1g}$ peaks, while also demonstrating these peaks at higher wavenumbers relative to the other samples. Alternatively, the first sample, which was mechanically exfoliated, demonstrated lower baseline and peak intensity than either of the solvent exfoliated samples.

Resultantly, the Raman spectroscopy method confirms a particle size consistent with mechanical exfoliation by using the solvents of the present invention.

B. Hafnium Oxide, Indium-Tin Oxide, Blue Indium-Tin Oxide, Zirconium Oxide, Zinc Oxide, Barium Titanate, Praseodymium (III, IV) Oxide Nanoparticle-sized particles of Hafnium Oxide, Indium-Tin Oxide, Blue Indium-Tin Oxide, Zirconium Oxide, Barium Titanate, Tin Oxide, Zinc Oxide and LSM were dissolved in thermodynamic equilibrium (providing a chi value of less than 0) in CHP. Similarly, nanoparticle-sized particles of Indium-Tin Oxide, Blue Indium-Tin Oxide, LSM, Tungsten Oxide, Praseodymium (III,IV) Oxide and Zirconium (IV) Oxide were dissolved in thermodynamic equilibrium (providing a chi value of less than 0) in NMP.

C. Few-Layer Graphene Exfoliation

Figure 4:
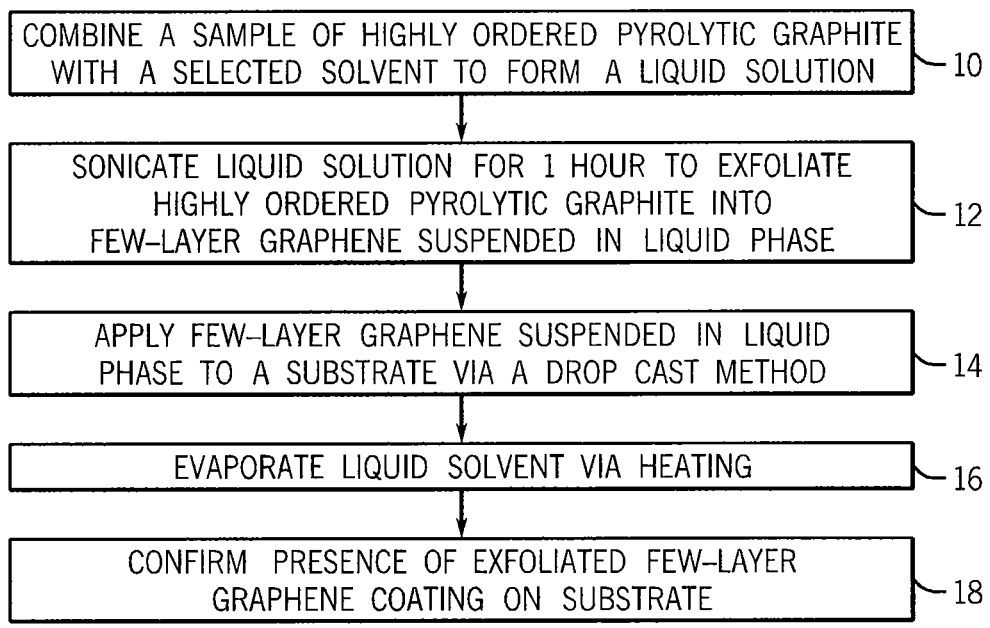
FIG. 4 is a flowchart of the steps of producing few-layer graphene.

Referring now to the flow chart of FIG. 4, the synthesis of few-layer graphene begins with a sample of highly ordered pyrolytic graphite (HOPG). The sample of HOPG solute is combined with a selected solvent per process block 10. The solvent may be one or more of various solvents, including: 1-cyclohexyl 2-pyrolidine (CHP), N-methyl-2-pyrrolidone (NMP), 2-Propanol (IPA), N, N-Dimethylformamide (DMF), Cyclopentanone (CPO), Cyclohexanone (CHO), or some combination thereof. The boiling points and surface tensions of these exemplary solvents are included below in Table 10.

TABLE 10

| Solvent | Boiling Point | Surface Tension at 20° C. |
|---|---|---|
| 1-cyclohexyl 2-pyrolidine (CHP) | 154° C. | 40 mN/m |
| N-methyl-2-pyrrolidione (NMP) | 202° C. | 40 mN/m |
| N,N-Dimethylformamide (DMF) | 153° C. | 37.10 mN/m |
| Cyclopentanone (CPO) | 131° C. | 32.80 mN/m |

Still referring to FIG. 4, the liquid solution of HOPG and select solvents undergoes sonication for 1 hour, until the HOPG is exfoliated in liquid phase to form few-layer graphene in liquid suspension per process block 12. The resultant solvent exfoliated few-layer graphene may subsequently be applied to a substrate such as silicone or silicon-dioxide via a drop cast method per process block 14. After heating the substrate to evaporate the liquid solvent (per process block 16), the remaining exfoliated few-layer graphene coating may be visualized under a scanning electron microscope to verify the formation of few-layer graphene coatings on the substrate per process block 18.

Example 2

Figure 5:
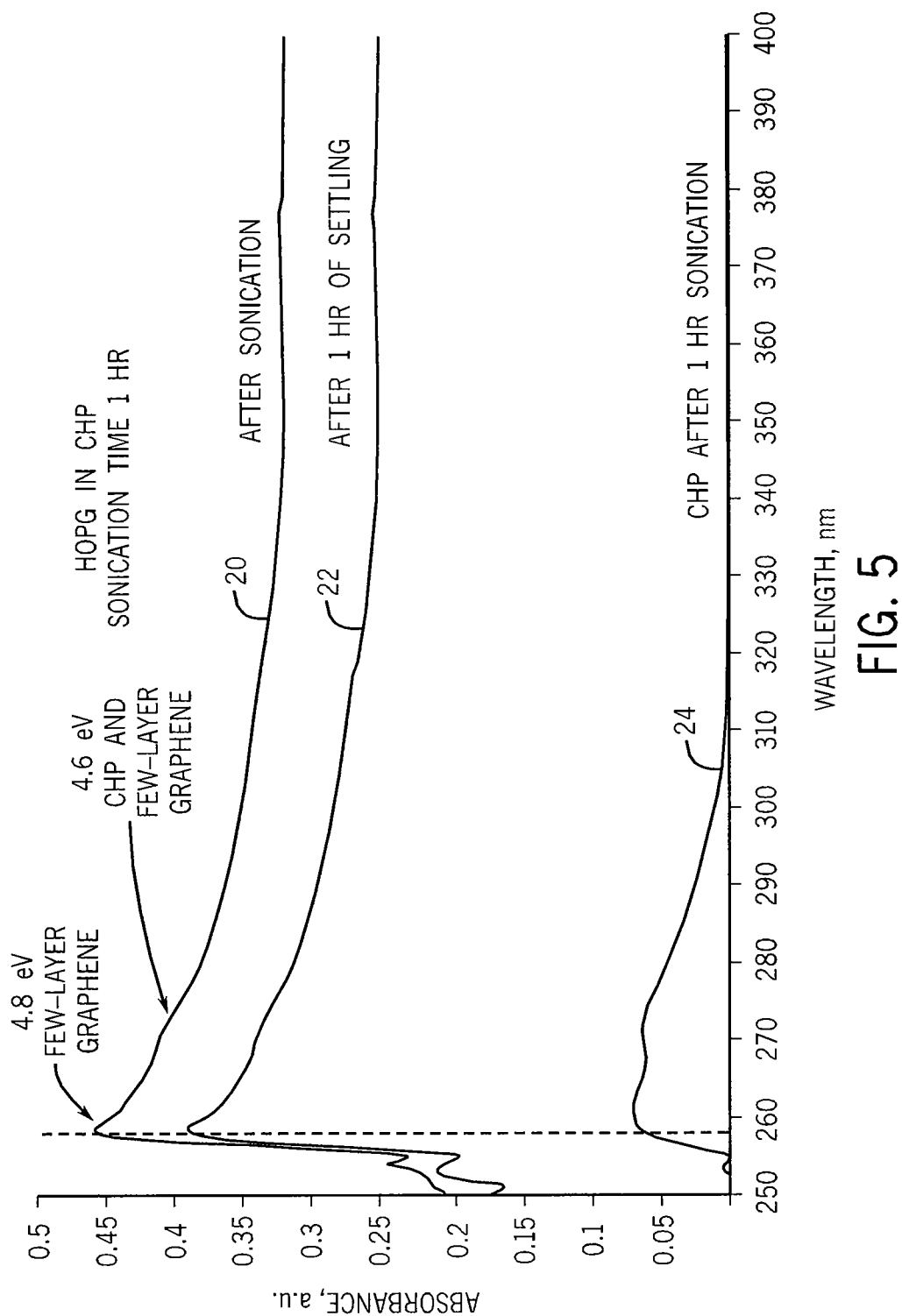
FIG. 5 is a graph showing sedimentation speed of graphene in a CHP solvent.

Referring now to FIG. 5, a graph is provided illustrating relative absorbance of a liquid suspension solution containing an HOPG solute in a CHP solvent after various time intervals, as obtained via ultraviolet-visible spectroscopy. A first plot line 20 indicates the absorbance of an HOPG/CHP solution immediately after 1 hour of sonication. At a wavelength of approximately 258 nm, the solution immediately removed from sonication exhibited an absorbance of approximately 0.45 a.u. The second line 22 on the graph indicates the absorbance of the same HOPG/CHP solution after 1 hour of settling which exhibits an absorbance of approximately 0.38 a.u. at the same approximate wavelength of 258 nm. These values are compared to the third line 24 of the graph which indicates an absorbance of only 0.6 a.u. at the approximate 258 nm wavelength of after 1 hour of sonication of pure CHP solvent. As such, it can be seen that the majority of exfoliated few-layer graphene remains within solution after 1 hour of settling.

Figure 6:
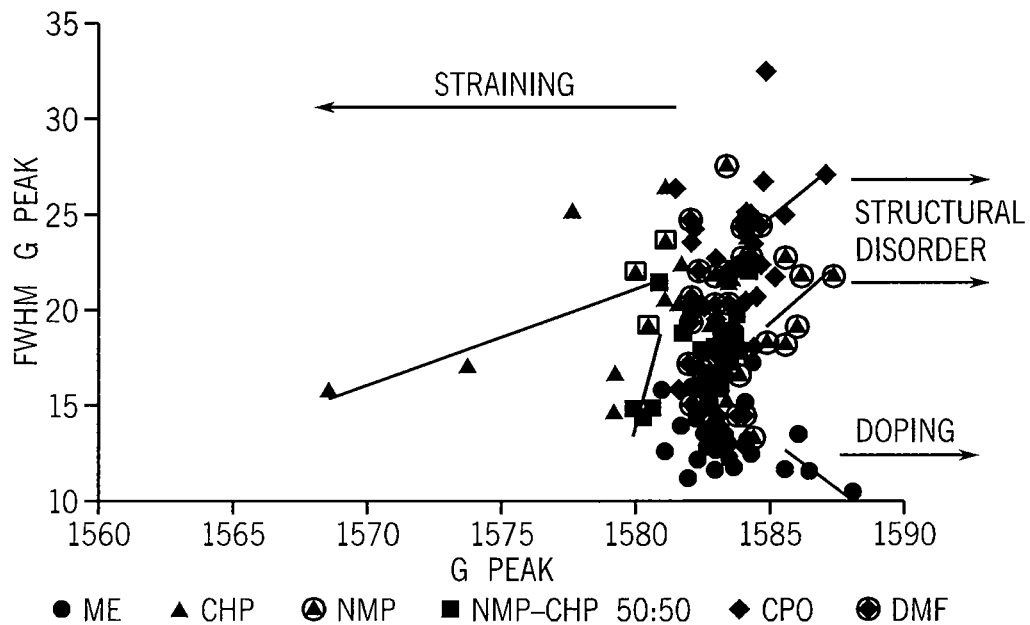
FIG. 6 is a graph showing structural disorder in few-layer graphene for different solvents as determined using Raman spectroscopy.

Referring now to the graph illustrated in FIG. 6, the structural disorder and straining of various samples of few-layer graphene are illustrated having been formed in solution with one of five distinct solvents, namely: CHP, NMP, CPO, DMF, and a mixture of 50% NMP and 50% CHP. FIG. 6 also includes data points corresponding to samples of few-layer graphene formed via mechanical exfoliation (ME), also known as the "scotch tape" method. The data displayed in FIG. 6 was obtained via Raman spectroscopy. As illustrated, few-layer graphene exfoliated in a solvent of 50% NMP and 50% CHP demonstrates less structural disorder and straining than either pure NMP or pure CHP solvents. Further, few-layer graphene exfoliated in a CPO solvent demonstrates less structural disorder than any of the other solvents tested.

Figure 7:
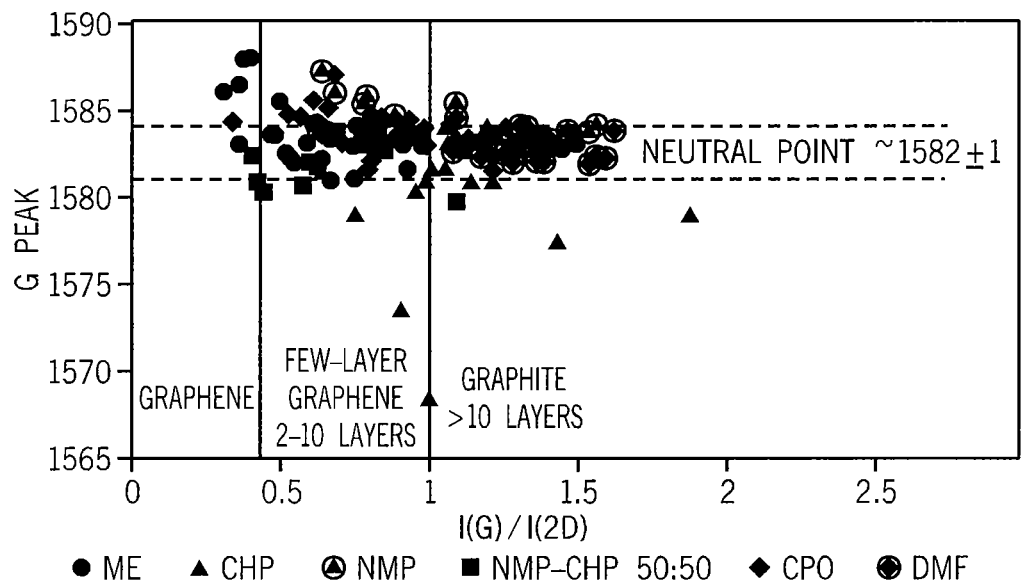
FIG. 7 is a figure similar to that of FIG. 6 showing graphene layer thicknesses obtainable with different solvents.
Figure 17:
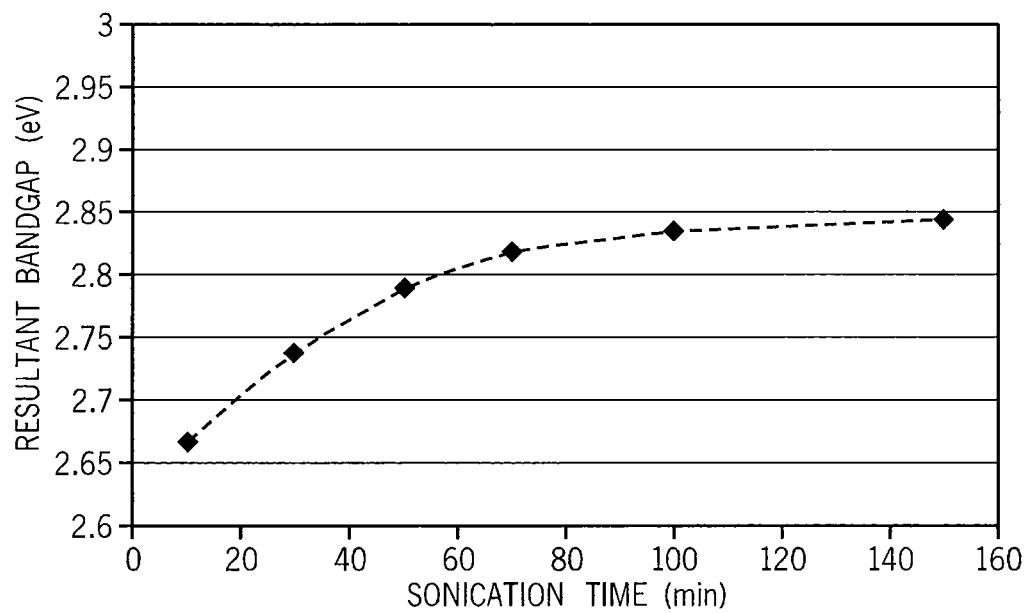
FIG. 17 is a plot of bandgap energies for the materials of FIG. 16 versus sonication time.

Referring now to the graph illustrated in FIG. 7, the number of layers of graphene produced according to the use of the five distinct solvents during liquid phase exfoliation is depicted. FIG. 17 also includes data points corresponding to samples of few-layer graphene formed via mechanical exfoliation (ME). This data was obtained via Raman spectroscopy. As illustrated, the use of the solvent CPO and the solvent mixture of 50% NMP and 50% CHP were capable of consistently producing graphene comprised of 2-10 layers. These results are comparable to the number of layers produced with mechanical exfoliation (ME). Alternatively, the use of solvents CHP, NMP, and DMF often produced graphene in excess of 10 layers.

Generally the amount of this order in few-layer graphene exfoliated in solvents can be controlled by the type of solvent. CPO and NMP-CHP exfoliates thinner flakes but CPO has less of this order comparable to other solvents. NMP-CHP produces flakes with less structural disorder or straining than pure NMP or pure CHP.

Therefore, the amount of structural disorder produced in few-layer graphene exfoliated in solvents and their thickness, i.e., number of layers, can be controlled by the solvent selected. Specifically, solvent CPO and a solvent mixture of 50% NMP and 50% CHP exfoliates thinner few-layer graphene sheets, while solvent CPO exhibits less structural disorder than other solvents. Therefore, by selecting the proper solvent, it will be possible to exfoliate few-layer graphene sheets of sufficient thinness and limited structural disorder as to utilize them in the formation of hybrid materials, such as fuel cell electrodes, as will be discussed in further detail below.

D. Combination Solventized Graphene and Other Materials

In another embodiment of the present invention, a selected solvent acts on a sample of graphite and exfoliated individual sheets of graphene composed of few-layers from the bulk graphite which is subsequently combined with solutes including metal oxides, metal chalcogenides, mixed metal oxides, and mixed metal chalcogenides to for hybrid materials. The size of the sheets of the resultant few-layer graphene that are exfoliated can be controlled through the selection of the particular solvent used, as solvents having surface tension values closer to the optimal value will be able to exfoliate larger area sheets, while solvents having surface tension values to either side of the optimal value will be less effective at solvating the graphite, resulting in the exfoliation of smaller area graphene sheets.

1. $TiO_2$ and Graphene Hybrid Material for High Efficiency Li-Ion Batteries

The present invention provides high-quality solvents for macromolecule and nanoparticle solutes, including, for example, solutes of metal oxides, metal chalcogenides, mixed metal oxides, and mixed metal chalcogenides. In one embodiment of the present invention, once in solution these metal oxides, metal chalcogenides, mixed metal oxides, and mixed metal chalcogenides may be more effectively utilized to form products such as Li-ion batteries. In this embodiment, $TiO_2$ has been targeted because it is a compound that prevents structural instabilities and provides fast Li insertion; the present invention is not limited to the use to $TiO_2$. $TiO_2$ is also an ideal choice for use in Li-ion batteries given that it is relatively abundant, environmentally benign and avoids electromechanical depositions of Li. However, $TiO_2$ is limited as an indirect semiconductor due to its limited electron mobility and limited performance at high charge/discharge rates. In an attempt to overcome these limitations, efforts have been made to combine graphene, which demonstrates excellent electron transportation, with the anatase crystalline configuration of $TiO_2$ through the use of Graphene Oxide (GO) or functionalized graphene sheets (FGS). Alternatively, the present inventors have dissolved anatase $TiO_2$ and combined it with a dissolved graphene to synthesize a hybrid material.

Via thermodynamic analysis, it was determined that solvents with a surface tension of approximately 40 $mJ/m^2$ were optimal for achieving exfoliation and stabilization of 2D material graphene. This dissolved graphene may be formed in accordance with the few-layer exfoliation methods, previously described. Furthermore, the solvents discovered by the present inventors have been determined to stabilize other macromolecule and nanoparticle solutes, including, for example, solutes of metal oxides, metal chalcogenides, mixed metal oxides, and chalcogenides, given that the solvents exhibit a similar surface tension. Accordingly, by optimizing the sonication and mixing parameters, the present inventors have successfully combined liquid phase exfoliated graphene and anatase $TiO_2$ into a pyrrolidone and then filtered the resultant hybrid supernatant.

Figure 8:
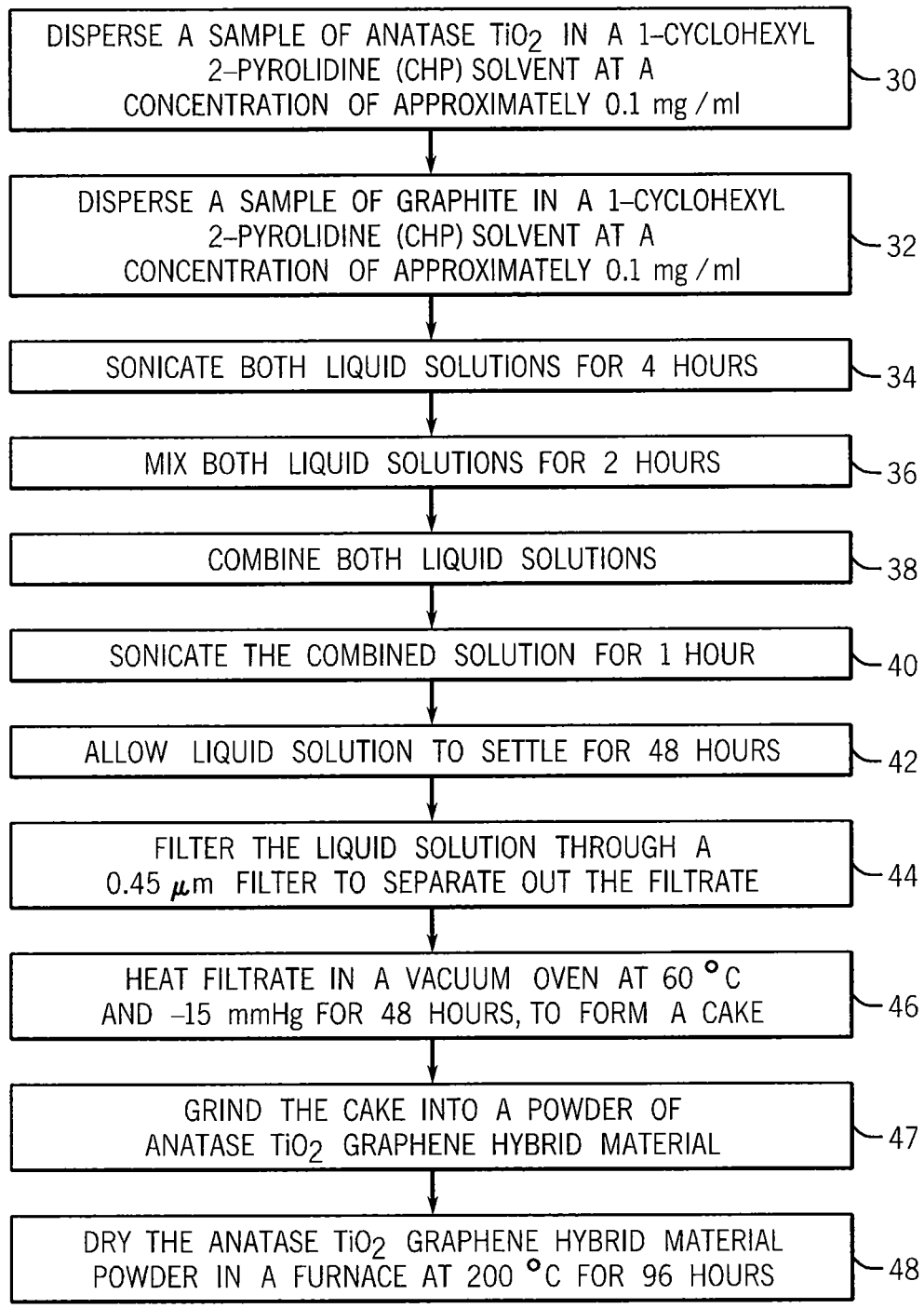
FIG. 8 is a flowchart showing steps of preparing a mixture of titanium dioxide and graphene per the present invention.

Referring now to FIG. 8, the synthesis of a $TiO_2$ and graphene hybrid material is provided in further detail. Initially, a sample of anatase $TiO_2$ was dispersed at a concentration of approximately 0.1 mg/ml in a 1-cyclohexyl 2-pyrolidine (CHP) solvent per process block 30. A sample of graphite was also dispersed at a concentration of approximately 0.1 mg·ml of 1-cyclohexyl 2-pyrolidine (CHP) solvent per process block 32. Each dispersion was sonicated for 4 hours in a sonic bath and subsequently mixed with a stir rod for 2 hours per process blocks 34 and 36. The dispersions were combined to form a combined dispersion (per process block 38) that was then sonicated for 1 hour per process block 40. The combined dispersion settled for 48 hours, per process block 42, and was then filtered through a 0.45 μm filter to separate out the filtrate per process block 44. The filter and filtrate were placed in a vacuum oven at 60° C. and −15 mmHg for 48 hours, until the filtrate formed a cake per process block 46. The cake was then removed from the vacuum oven and ground into a powder per process block 47. The powder, i.e., anatase $TiO_2$ and graphene hybrid material, was dried in a furnace at 200° C. for 96 hours per process block 48.

The anatase $TiO_2$ and graphene was analyzed via scanning electron microscope (SEM) and compared to a SEM scan of a known result synthesized through the use of Graphene Oxide (GO), to successfully confirm hybridization. The resultant anatase $TiO_2$ and graphene hybrid material was then used to form a Li-ion battery electrode and a generic electrode sheet, in accordance with the formation of $TiO_2$ nanowires as will be discussed in further detail below.

E. $TiO_2$ Nanowire in Stabilized Soluble Solution

The stabilized soluble solution of the present invention may alternatively be a solution of a metal oxides, metal chalcogenides, mixed metal oxides, and/or mixed metal chalcogenides capable of forming a nanowire or nanotube. In one embodiment of the present invention, nanowires were synthesized from an anatase $TiO_2$ solution. Having exhibited a higher surface area, faster Li-insertion, a stronger resistance to stain induced by Li-intercalation/deintercalation, and improved charge carrier transport, $TiO_2$ is being targeted for use in photocatalytics, energy storage and gas sensors. In light of this high demand, the present inventors have developed a process for synthesizing a nanowire from an anatase $TiO_2$ liquid suspension solution. While alternative methods of synthesizing $TiO_2$ nanowire have involved the use of a low-temperature hydrothermal synthesis using alkaline environments, such an approach resulted in extreme bundling of the produced nanowires and/or nanotubes. Alternatively, the current process is particularly well suited for forming 1D $TiO_2$ materials in a disperse and debundled configuration.

Figure 9:
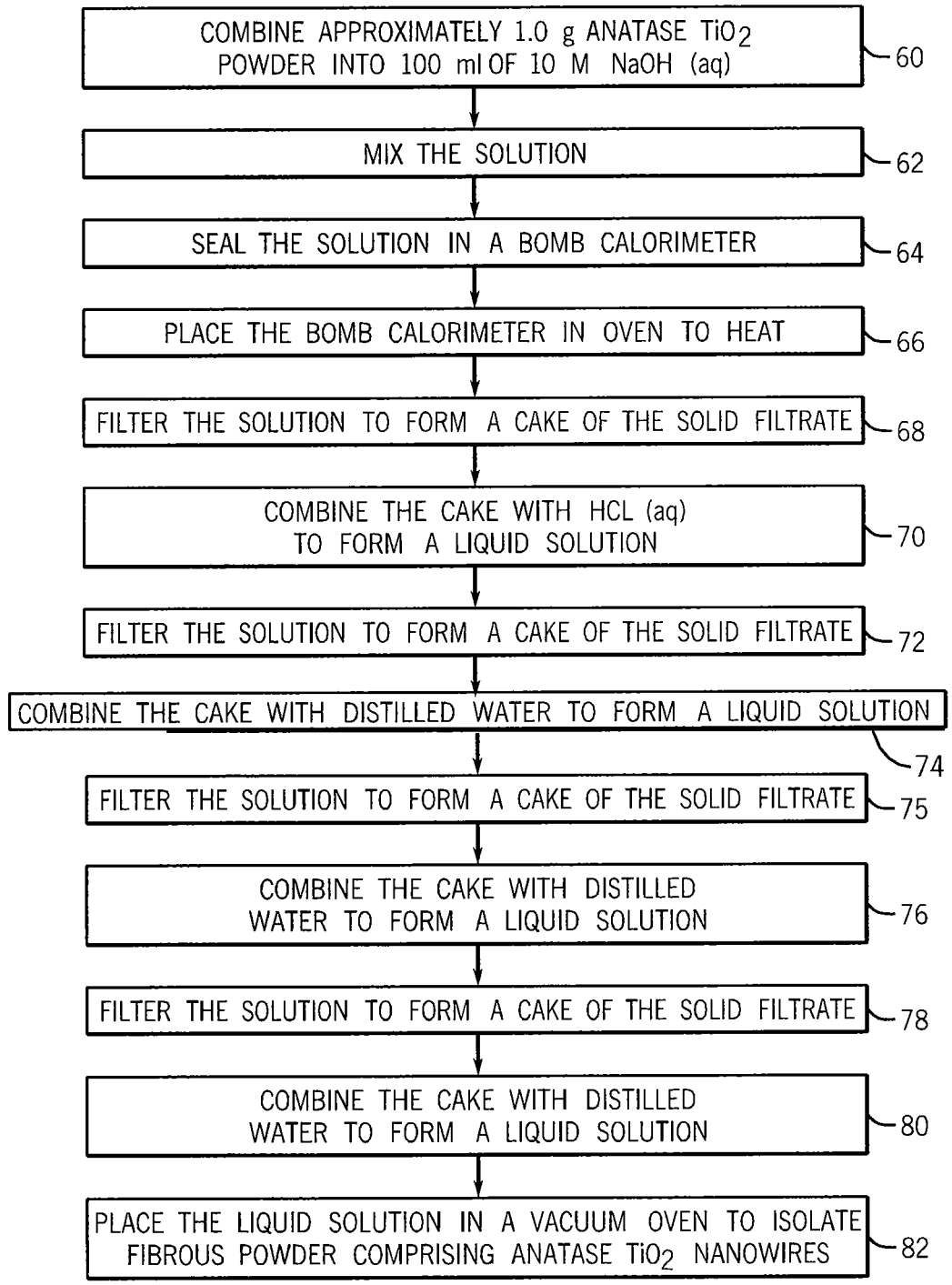
FIG. 9 is a flowchart showing preparation of titanium dioxide nanowires per the present invention.

Referring now to FIG. 9, the synthesis of an anatase $TiO_2$ nanowire is provided in further detail. Initially, 1.01 g of anatase $TiO_2$ powder was placed into 100 Ml of 10 M NaOH (aq) per process block 60. The mixture was then placed in an Erlenmeyer flask, and stirred for 3 hours per process block 62. The mixture was then placed into a bomb calorimeter and sealed per process block 64. The bomb calorimeter was placed in a 208° C. oven for 24 hours per process block 66. After heating, the bomb calorimeter was removed from the oven and allowed to cool to room temperature. The mixture was subsequently filtered with a 0.45 μM nylon filter disc until the remaining solid filtrate formed a cake per process block 68. The cake was broken up and placed into a 0.1 M HCL (aq) solution and gently mixed per process block 70. This solution was again filtered with a 0.45 μm nylon filter disc until the remaining solid filtrate formed a cake per process block 72. The filtrate was filtered twice more by breaking up the cake and placing it in a beaker of distilled water per process blocks 74-80. Finally the filtrate was placed in into a beaker of distilled water and placed in a 75° C. and −20 in Hg vacuum oven for 12 hours to isolate a fibrous powder comprising anatase $TiO_2$ nanowires per process block 82.

A sample of the resultant filtrate, i.e., anatase $TiO_2$ nanowires, was analyzed and showed $TiO_2$ nanowires in highly bundled configuration via scanning electron microscope (SEM). A Raman spectra of the $TiO_2$ nanowires was obtained using a T64000J-Y Horiba Raman spectrometer and a 532 nm ND:YAG laser for 5 accumulations of 20 seconds each. The resulting peaks were not characteristic of anatase $TiO_2$; they indicate that the fibrous powder comprising anatase $TiO_2$ nanowires included some contaminants and was not entirely rinsed and/or dried.

Multiple solution suspensions of the synthesized anatase $TiO_2$ nanowires and nanotubes were then created. A sample of the fibrous powder comprising anatase $TiO_2$ nanowires was first milled using a mortar and pestle. The milled sample of anatase $TiO_2$ nanowires was then placed directly into suspension in four distinct solvents: N-methyl-2-pyrrolidone (NMP), isopropyl alcohol (IPA), 1-cyclohexyl 2-pyrolidine (CHP), and ethanol. Each suspension was then mixed vigorously for 30 minutes and then sonicated for 1 hour at low energy. Each suspension was observed for two weeks following sonication. The synthesized anatase $TiO_2$ nanowires in 1-cyclohexyl 2-pyrolidine (CHP) solution appeared cloudy, indicating that the synthesized anatase $TiO_2$ nanowires had not settled out of suspension after a period of two weeks.

Figure 10:
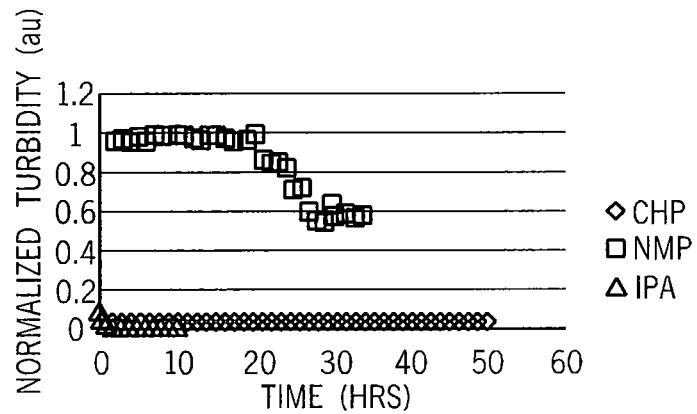
FIGS. 10-12 are plots of turbidity versus time for different solvents with the plots of FIG. 11 and FIG. 12 having expanded vertical axes.
Figure 11:
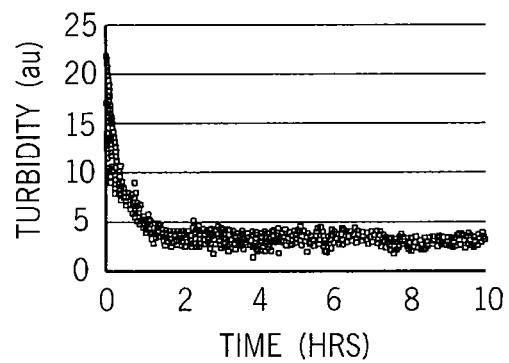
Figure 12:
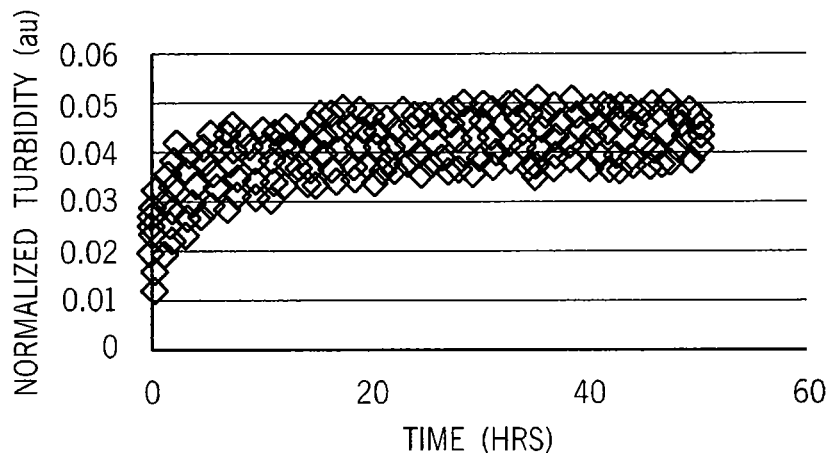

Referring now to FIGS. 10, 11, and 12, the synthesized anatase $TiO_2$ nanowire solutions containing CHP, NMP and IPA solvents were analyzed using a fiber optic UV-Vis sedimentation setup and a 532 nm ND:YAG laser sedimentation instrument, measuring both scattering and absorption. During analysis, the three samples were maintained at a constant temperature of 20° C. to limit variable convection. FIG. 10 is a graph depicting the normalized turbidity (a.u.) of the synthesized anatase $TiO_2$ nanowire over a time period of 50 hours after sonication for the three samples. As seen in FIG. 10, the normalized turbidity of the NMP solution is substantially greater than the CHP and IPA solutions due to its higher concentration. However, as is consistent with the chart of FIG. 11 and detailed further in the chart of FIG. 12, the CHP solution demonstrated negligible sedimentation during the course of 50 hours, relative to both the NMP and IPA solutions. Alternatively, as detailed in the chart of FIG. 11, the majority of synthesized anatase $TiO_2$ nanowire has fallen out of suspension in the IPA solution, after only 2 hours. Accordingly, this alternative embodiment indicates that CHP is capable of maintaining a stable suspension of debundled synthesized $TiO_2$ nanowires and/or nanotubes over a prolonged period of 2 weeks, and at least 50 hours.

F. Anatase and Rutile $TiO_2$ Separation

Titanium dioxide occurs both naturally and synthetically in three mineral forms, two of which are anatase and rutile. While having the same chemical formula, $TiO_2$, these two distinct mineral forms differ predominantly in their respective crystal symmetry. As a result of these intrinsic differences anatase and rutile Titanium dioxide offer different functional characteristics in various application examples considered in the present invention, such as photocatalytics, batteries, electrodes, etc. As such, a process for isolating anatase and rutile Titanium dioxide from a mixed sample is desired, such that these distinct forms may be utilized individually.

In light of this need, the present inventors have developed a process for isolating anatase TiO2 in a liquid suspension solution from a sample comprised of both anatase and rutile Titanium dioxide. Specifically, a solvent is selected that exhibits an affinity for stabilizing anatase TiO2 nanoparticle in solution and a relatively lower affinity for stabilizing rutile TiO2 nanoparticle in solution solutes. The solvent may be one or more of various solvents, including: 1-cyclohexyl 2-pyrolidine (CHP), N-methyl-2-pyrrolidione (NMP), 2-Propanol (IPA), N, N-Dimethylformamide (DMF), Cyclopentanone (CPO), or some combination thereof. A sample of mixed anatase and rutile TiO2 is placed in a mixture of the selected solvent. The mixture was subsequently sonicated and/or stirred until the TiO2 nanoparticle were placed into aqueous suspension. The suspension was then allowed to rest until the rutile Titanium dioxide precipitated out of the suspension (approximately 24 hours). At this time, the container of anatase TiO2 was visibly cloudy with no apparent precipitate while the container of rutile TiO2 was visibly clear with a white precipitate at the bottom of the container. The resultant supernatant, containing the anatase TiO2 in liquid suspension was extracted. The solvent was then extracted and the isolated anatase TiO2 nanoparticle were dried by vacuum oven, or other means disclosed herein. Of course, this method may also be applied to the isolation of rutile TiO2 by isolation of the precipitate instead of the supernatant.

It is expected that this technique will work to separate other crystalline materials having differences in surface energy analogous to those of anatase TiO2 and rutile TiO2.

G. Li-Ion Battery and Ultracapacitor Electrodes

Figure 13:
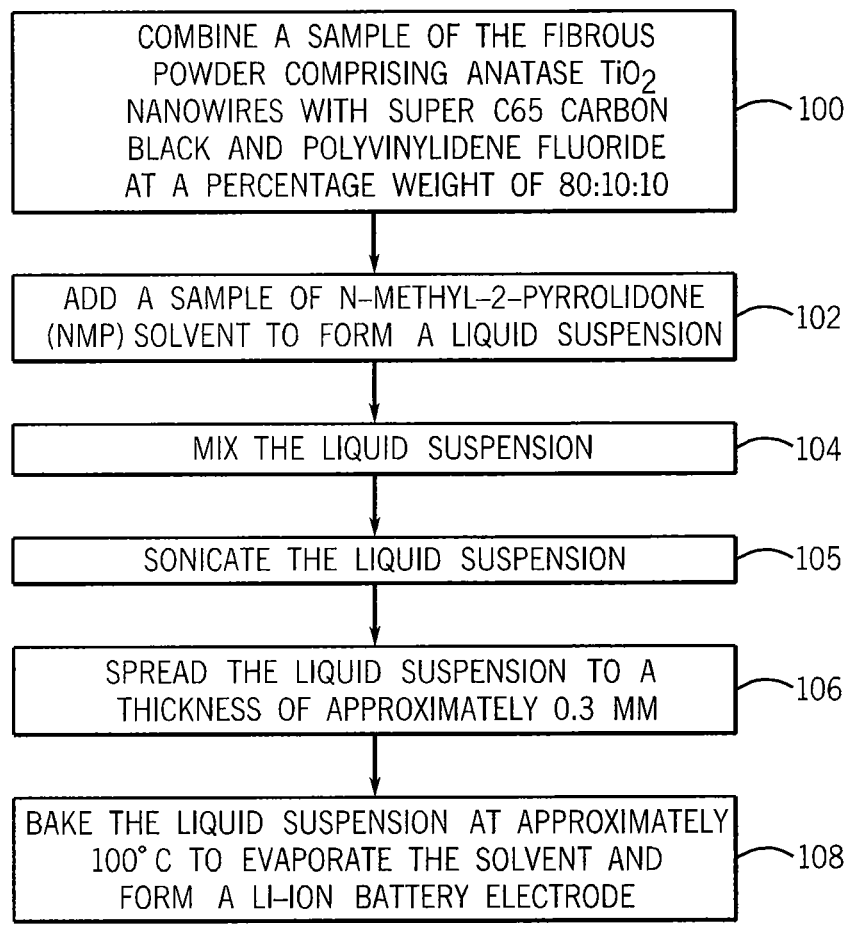
FIG. 13 is a flowchart of the steps of preparing an electrode of titanium dioxide and graphene using a carbon predicate material.

Referring to FIG. 13, the synthesized anatase $TiO_2$ nanowires, as discussed above, may alternatively be deposited on the surface of a conductor to form a Li-ion battery electrode. Such an electrode may be formed by means of placing 0.31 g of the fibrous powder comprising anatase $TiO_2$ nanowires into a vial with Super C65 carbon black and polyvinylidene fluoride (PVDF binder) at a percentage weight of 80:10:10, respectively, per process block 100. Next, 6.9 mL of the solvent N-methyl-2-pyrrolidone (NMP) was then added to the vial, and the resultant solution was mixed vigorously for 5 minutes and then sonicated for 10 minutes per process blocks 102-105. Immediately after sonication, the solution was spread across aluminum foil at a thinness of 0.3 mm per process block 106. The aluminum foil was then baked at 100° C. in an oven, to form a Li-ion battery electrode per process block 108. SEM images of a Li-ion battery electrode containing anatase $TiO_2$ nanowires formed in accordance with an alternative embodiment of this invention showed significantly less bundling and fewer impurities compared to the previously described synthesized anatase $TiO_2$ nanowires which were not placed in a stabilized soluble solution. The resultant Li-ion battery was cycled continuously using a Gamry 3000 potentiostat using c/5, 1C, 2C, 3C, 10C, 20C and 30C based upon the theoretical capacity of 168 mAh/g of rutile $TiO_2$. The voltage window was from 1.0 V to 3.0 V and between cycles there was no voltage finished for current equilibrium.

In addition to $TiO_2$ nanowires, as discussed above, a solute of nanosilica has also been shown to form a suspension in a selected solvent, and resultantly formed an electrode suitable for use in battery applications.

H. Coating and Films of Anatase $TiO_2$ Soluble in CHP

In yet another alternative embodiment, the stabilized soluble solution, i.e., suspension, of a metal oxide, metal chalcogenide, mixed metal oxide, and/or mixed metal chalcogenide may be formed into a coating or film. As discussed in further detail below, such coating or films may be used in a wide variety of applications. Exemplary films were synthesized by creating a suspension of $TiO_2$ solute suspended in a various solvents, including ethanol, distilled water, CHP and NMP. However, it is considered within the scope of this invention that suspensions of other metal oxides, metal chalcogenides, mixed metal oxides, and/or chalcogenides, such as $MoS_2$, PBS, CdSe, and $Cu(In,Ga)Se_2$ are capable of forming a similar coating or film. $TiO_2$ films can be useful for creating high refractive index thin films and thin-film solar cells.

Specifically, a sample of anatase $TiO_2$ was combined with each solvent, e.g., ethanol, distilled water, toluene, butanone, and NMP, at a concentration of approximately 0.5 mg/mL. The anatase $TiO_2$ sample utilized in these embodiments was manufactured by Evonik Deussa, according to the AEROSIL® process, and designated as TiO₂ P 25. These solutions were mixed on a Vortex mixed in 1 ounce vials for two minutes, and then sonicated for 30 minutes. The solutions were then allowed to settle for three days. 2 mL of each solution were then placed in a centrifuge tube and centrifuged at 2000 rpm for 100 minutes. The resultant supernatants were removed to form films which were subject to atomic force microscopy, scanning electron microscopy, and UV-Vis absorption analysis.

Figure 14:
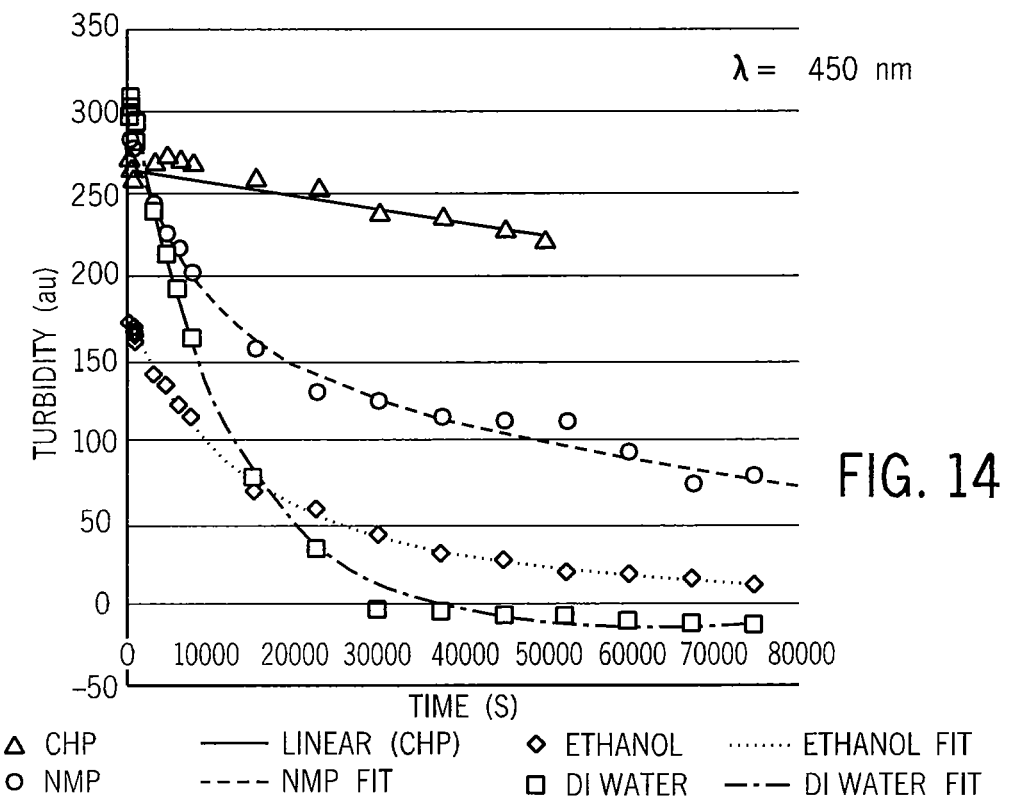
FIG. 14 is a graph showing sedimentation speed for different solvents and an anatase $TiO_2$ solute.

Referring now to FIG. 14, a graph is presented depicting the sedimentation data for the four suspensions of anatase TiO₂ in ethanol, distilled water, CHP, and NMP solvents, in accordance with the above method. At a wavelength of 450 nm, the solution of TiO₂ exhibited a substantially higher turbidity than the three remaining solvents, indicative of suspended TiO₂ nanoparticles. While the CHP solvent was capable of maintaining TiO₂ nanoparticles in solution for a prolonged period following centrifugation, TiO₂ nanoparticles rapidly fell out of suspension in both ethanol and distilled water solvents.

Figure 15:
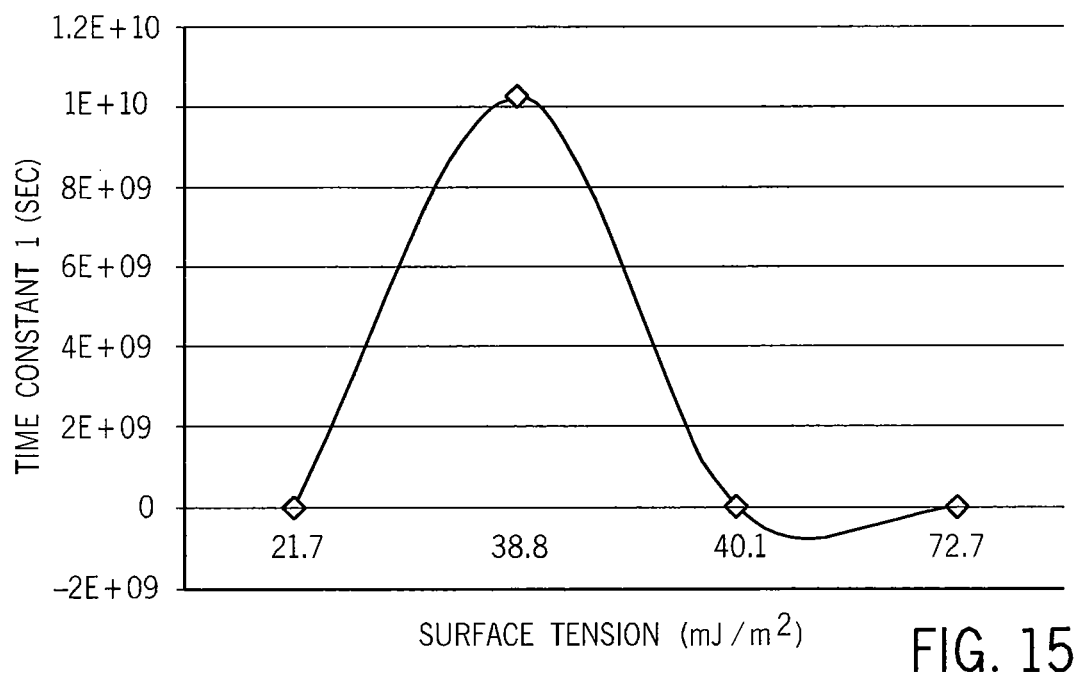
FIG. 15 is a graph of a sedimentation time constant versus surface tension of the solvent.

Referring to FIG. 15, the time constant of the sedimentation for these different solvents may be plotted against the surface tension of the solvents to reveal a relationship which may direct the identification of even better solvents.

An additional series of suspensions were prepared to analyze the sedimentation of anatase TiO₂ in each solvent, e.g., ethanol, distilled water, CHP, and NMP. These four solutions were initially prepared at a concentration of approximately 0.2 mg/mL. The four solutions were sonicated for 30 minutes and immediately placed into a UV-Vis sedimentation system. The UV-Vis sedimentation system was operated for 100 hours, to observe the sedimentation of each suspension as previously discussed.

Sonication and bandgap studies were subsequently performed on a suspension of TiO₂ and CHP, initially as stock solution of P25 TiO₂ and CHP at a concentration of 1.004 mg/mL. The suspension was mixed via a Vortex Mixer and sonicated for 30 minutes to dissolve large agglomerates and remove bubbles. The stock solution was then divided into seven 1 ounce vials for sonication at approximately 3 W input power for 10, 30, 50, 70, 100, 150 and 300 minute periods respectively. Following sonication, 1 mL was removed from each vial and combined with 10 mL of pure CHP. Seven thin films were then prepared from these seven samples by drop casting the TiO₂ P 25 and CHP suspensions onto preheated silicon substrates at 125° C., to promote uniformity. The substrates were then dried at 175° C. and −15 in Hg in a vacuum oven for 2 hours. After cooling for 2 hours, the samples were analyzed via Raman spectroscopy and atomic force microscopy.

Figure 16:
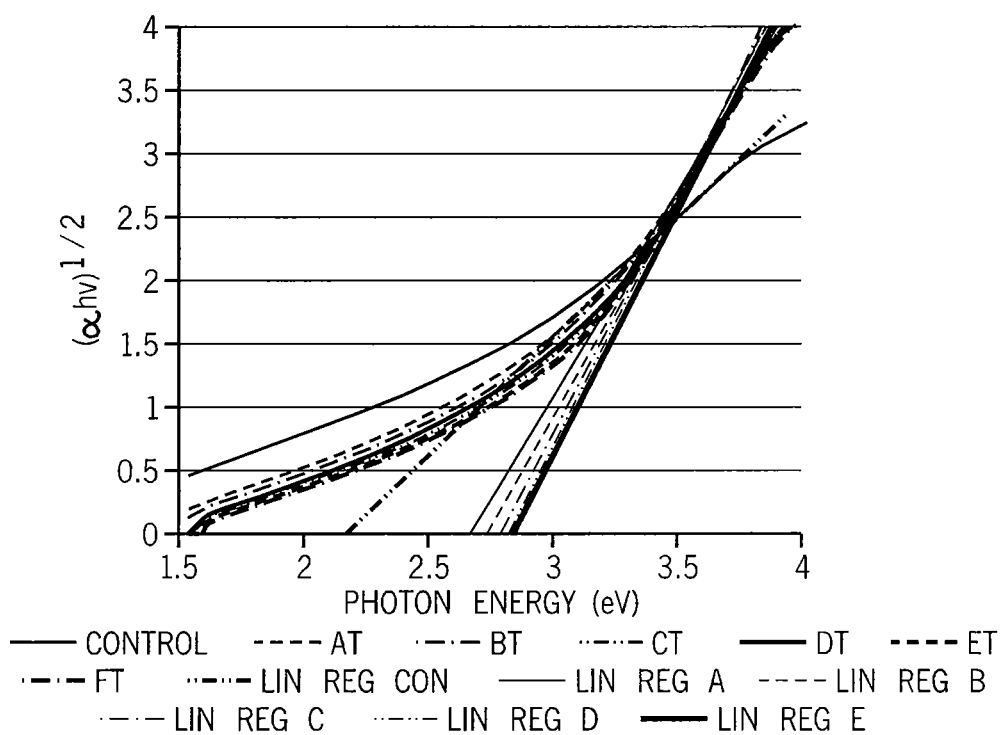
FIG. 16 is a plot of bandgap energies for different titanium dioxide films prepared using CHP.

Referring now to FIG. 16, the bandgap energies for the films synthesized from the seven TiO₂ P 25 and CHP samples of differing sonication times was estimated in accordance with the following Equation (5):

$$\alpha(\eta\omega) \propto \frac{\sqrt{\eta\omega - E}}{\eta\omega} \quad (5)$$

where E is the bandgap energy, h is the reduced Planck's constant and □* is the incident photon frequency. As see in the graph of FIG. 11, the indirect bandgap energy determination of seven TiO₂ P 25 and CHP samples is illustrated as the point when the linear fit of each sample intercepts the x-axis. Specifically, the bandgap energy determination of various TiO₂ P 25 and CHP samples is between 2.0 and 3.0 eV, and much lower than anticipated.

Referring now to the graph of FIG. 17, the bandgap energies for the various samples of TiO₂ P 25 and CHP are plotted versus sonication time in minutes. As can be seen by the trend line, measured bandgap energies demonstrate a trend approaching an upper limit at approximately 2.85 eV. This limit may represent the size of the TiO₂ P 25 nanoparticles in CHP solvent, approaching a lower limit in size based upon excitation energy. This trend illustrates a decrease in particle size with sonication in the presence of a solvent presenting a generalizable method for reducing particle sizes in nanomaterials.

Figure 18:
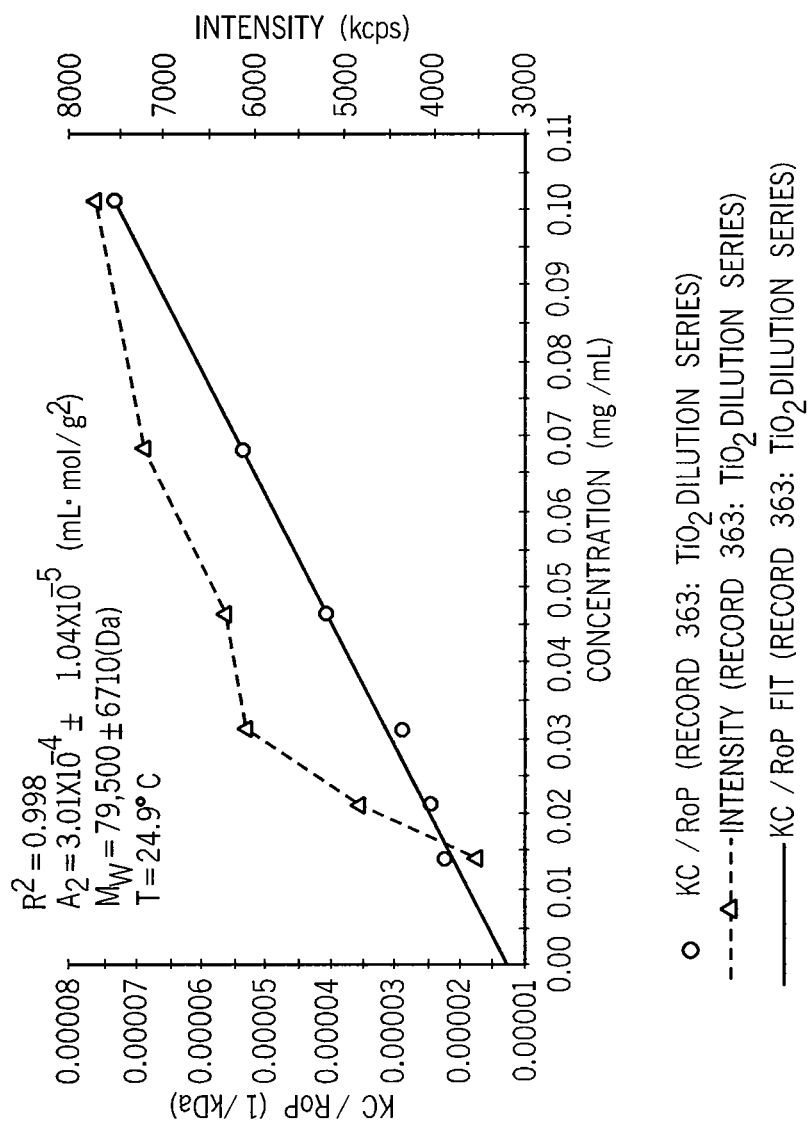
FIG. 18 is a Debye plot indicating the thermodynamic equilibrium of the solution of titanium dioxide in CHP.

Referring now to FIG. 18, a graph is presented, depicting a Debye plot for the thin films created from the suspension of TiO₂ P 25 in a CHP solvent created according to the above method. The graph indicates a negative solubility parameter, chi. This negative solubility parameter is indicative of a thermodynamically favorable suspension.

I. Polymer Films and Composites

Figure 19:
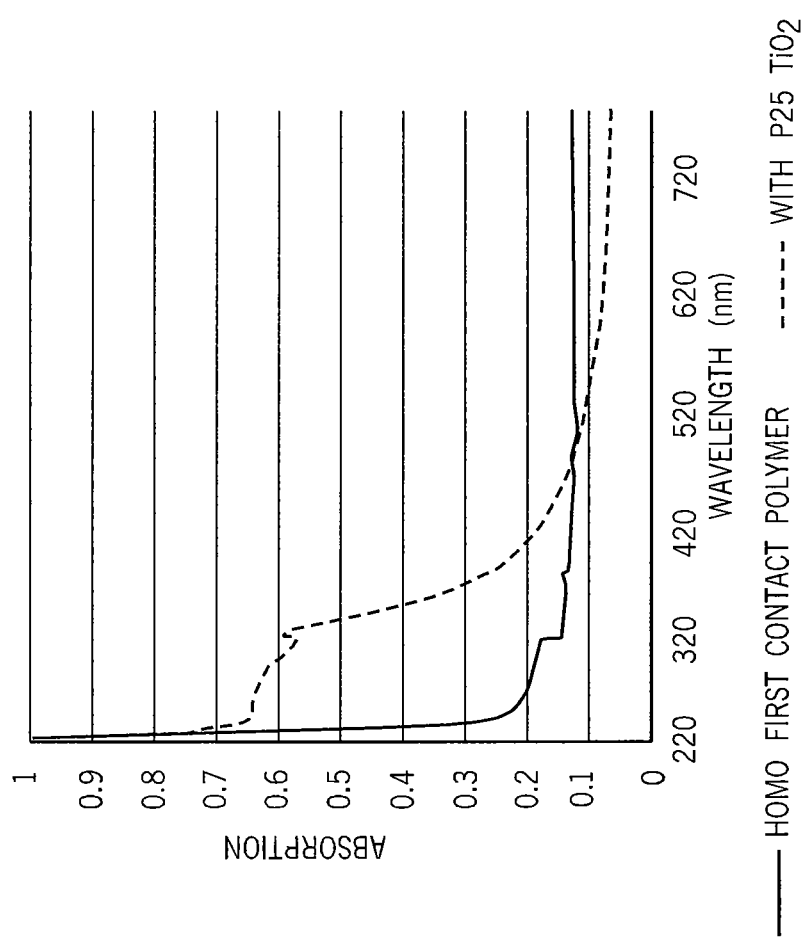
FIG. 19 is an ultraviolet absorption plot of a polymer having solvent-sized titanium dioxide incorporated therein.

In a method similar to the formation of thin films above, polymer matrix films were generated by directly mixing a suspension of TiO₂ P 25 and CHP with First Contact cleaning polymer, which were then spun coat onto glass slides and dried in a vacuum oven for 5 hours at 65° C. and −15 in Hg. The resultant polymer matrix films were removed from the glass slides and analyzed via UV-Vis absorption spectroscopy. As seen in FIG. 19, which compares the UV-Vis absorption of a pure First Contact Polymer film commercially available from Photonic Cleaning Technologies with one containing TiO₂ P 25, the TiO₂ P 25 polymer shows favorable UV absorption and some activation in the visible light range. The First Contact Polymer comprises a mixture of:

FORMAL GLYCOL 10-40% mass content,
BIS(METHOXY)METHANE 10-30% mass content,
ETHYL ALCOHOL 30-50% mass content,
ACETONE 10-30% mass content,
ETHYL LACTATE<10% mass content, and
ETHYL ACETATE<10% mass content.

Anatase TiO2 is also thermally stable, non-toxic, absorbs ultraviolet light, and demonstrates a relatively low absorption of light in the visible spectrum. As such, TiO2 has UV-protective properties which are desirable in the formation of polymer composites and films in which the TiO2 CHP suspension is polymerized or solidified into the three-dimensional materials or thin films. Such polymer candidates include liquid phase polymers, which can be mixed directly with the TiO2 CHP suspension. The formation of the polymer composite occurs by placing the selected nanoparticle in a solvent to form a suspension, such as a TiO2 CHP suspension as has been described above. The suspension is subsequently combined with a polymer, such as a liquid phase polymer. Examples of polymers which have been successfully used to form nanoparticle suspended polymers include: first contact polymer, polyurethane, styrene, and epoxy resins. The solvent is then removed or extracted from the polymer, while the selected nanoparticles remain suspended within the polymer. This method may be utilized to form both polymer composites and polymer films.

Furthermore, due to the previously discusses identification of the nanomaterial "material resonance", it is possible to accurately identify the intrinsic property of an ideal polymer matrix for a given soluble nanoparticle material. The resultant polymer composite or film will exhibit a more uniform distribution of the soluble nanoparticle material to maximize performance. As in the example of anatase TiO2 and its UV-protective properties, once the solvent has been evaporated, the resultant polymer matrix may exhibit significantly improved UV-protective properties over comparable polymer composite due to improved dispersion of TiO2.

In addition to anatase TiO2, this polymer formation method has been applied to suspensions of the following nanoparticle solutes, to form polymer composites and films: Lead (II) Zirconate, Bismuth(III) Selenide, Calcium Titanate Nanopowder, Lithium Cobalt Phosphate Spinel Powder, Terbium (III, IV) Oxide Nanopowder, Lithium Titanate Spinel Nanopowder, Cadmium Selenide, Cadmium Telluride Powder, Indium Tin Oxide Nanopowder, Zirconium(IV) Oxide Nanopowder, Anatase Titanium (IV) Oxide Nanopowder, Rutile Titanium (IV) Oxide Nanopowder, Zinc Oxide Nanopowder, Copper(II) Oxide Nanopowder, Iron (III) oxide Nanopowder, Iron (II,III) oxide Nanopowder, Cadmium Sulfide Powder, Barium Titanate Nanopowder, Praseodymium (III,IV) Oxide Nanopowder, CIGS Powder of a 325 mesh size, Hafnium Oxide (HfO2) Nanopowder, Indium Tin Oxide (In2O3:SnO2=90:10) Nanopowder, Aluminum Oxide (Al2O3) Nanopowder, Tin Oxide (SnO2) Nanopowder, Terbium (III,IV) Oxide Nanopowder, Nanoclay such as Closite® as manufactured by Southern Clay Products, Inc., Blue ITO (Indium Tin Oxide), Vanadium Oxide, Lead Zirconate Titanate (PZT), Bi2Te3, Sb2Te3, Hexaboron Nitride (HBN), MoS2, and WS2. The solvents utilized to suspend these various nanoparticle solutes in suspension, prior to combining with a polymer component, were identified individually in accordance with the methods disclosed above, and may include but are not limited to DMF, CPO, CHP, NMP and mixtures thereof. These various nanoparticle solute suspensions were subsequently combined in polymers including: first contact polymer, polyurethane, styrene, and epoxy resin, prior to extraction of the solvent to form the resultant polymer composites and films.

In use, films, coatings and composites formed from the suspensions discussed above, including a coating or films formed from the exemplary solution of a $TiO_2$ nanoparticle solute suspended in CHP solvent, offer many diverse applications. The applications will be discussed in further detail below.

III Prophetic Product Applications

A. Solar Cells

As an effective photocatalyst, anatase $TiO_2$ is a wide band gap semiconductor that exhibits excellent optical transmission with a high reflective index and high dielectric constant. While others have attempted to improve its solar absorbance by reducing its band gap energy of 3.2 eV with the aid of a dopant, such as cobalt, the present suspension may improve solar absorbance without the need of a dopant. For example, the addition of graphene sheets may be introduced to the $TiO_2$ CHP suspension to increase the photoelectrocatalyst properties of the hybrid mixture, when formed as a film.

B. Paint

Due to its high absorbance of ultraviolet light, a $TiO_2$ CHP suspension may be incorporated into a paint or alternative optical coating. A paint can be prepared by creating a suspension of $TiO_2$ according to the present invention and mixing it with a resin or alternate binder. The solvent of the $TiO_2$ suspension, such as CHP, may then be extracted or, alternatively, may form the solvent component common to liquid paint. Additional color pigments may be combined with the white pigments of $TiO_2$. The resultant paint, which after application and evaporation of the solvent, may exhibit improved UV-protection and durability.

C. Sunscreen

A $TiO_2$ CHP suspension may be incorporated into topically applied solutions to provide an ultraviolet sun block. As previously indicated, $TiO_2$ exhibits a high absorbance of ultraviolet light and a low absorption of light in the visible spectrum. A sunscreen can be prepared by creating a suspension of $TiO_2$ according to the present invention and mixing it with natural or synthetic oils, including, for example, cocoa butter or the like or carrier fluids such as PEG-6. The solvent, such as CHP, may then be extracted, for example, by evaporation, preserving the $TiO_2$ in a colloid or viscous suspension to be applied as a sunscreen to the skin. Alternatively the $TiO_2$ may be incorporated into matrix materials such as thin plastic films to provide ultraviolet resistance to degradation of the underlying polymer.

D. Semiconductor Applications

A $TiO_2$ CHP suspension, as well as suspensions including alternative oxide and chalcogenide solutes, such a $MoS_2$, PBS, CdSe, and $Cu(In,Ga)Se_2$ are capable of forming a similar coating or film with semiconductor characteristics. As a result of varying the oxide or chalcogenide in suspension, it is possible to select a compound with a particular doping level, shape and particle size. Furthermore, transitional metal chalcogenides form various nanostructures, including inorganic nanotubes, fullerene-likes, nanowires, and others. In the context of semiconductor-related applications and electronic devises, films and/or coating formed from the afore mentioned suspensions may include, but are not limited to, phase change data storage materials such as DVDs, superconductors, thermoelectric devices such as Peltier elements, piezoelectric devices, and electrostatic devises such as nano-generators. The presently invented suspensions may also be used to form films or coatings for electro-optic sand and nonlinear electronic properties such as diodes, transistors and thin transistor films for use in thin film transistor liquid crystal displays and photovoltaics.

E. Energy Storage

As discussed above, synthesized anatase $TiO_2$ nanowires may alternatively be deposited on the surface of a conductor, such as graphene sheets to form a Li-ion battery electrode or ultracapacitor. In accordance with this method, synthesized anatase $TiO_2$ nanowires and other soluble nanomaterials may alternatively be deposited on the surface of a conductor to form batteries, capacitors, and/or ultracapacitor materials. Due to the increased surface area of the nanomaterials, each of these applications would exhibit improved storage capacity. Furthermore, selection of the desired solvent may allow precise control over the size and aggregated distribution of the nanomaterial to control formation of such batteries, capacitors, and/or ultracapacitor materials.

F. Nanomaterials Recycling

In the context of aftermarket recycling, administration of a highly effective solvent, such as those presently identified, would allow removal of nanomaterials from consumer products such as displays or energy storage devices for subsequent reuse. Similarly, once the nanomaterials have been extracted from the solvent, the solvent may also be recycled and reused.

Generally, the present invention can be expected to improve the above processes that use metal oxides, metal chalcogenides, mixed metal oxides, and/or chalcogenides and that normally require surfactants or dispersants and extensive mechanical agitation by either eliminating the surfactants, dispersants, and agitation or augmenting them. The ability to produce a true thermodynamic solution with a significant concentration of these materials leads to expected improvements in a variety of processes in which these solutes are dispersed in a "pristine" form, meaning without additional functionalization, surfactant or dispersion coatings. The present system can be distinguished from systems suspending macromolecules in materials identified as solvents in a general sense (that is, they serve as solvents in some contexts) because such suspensions typically do not create equilibrium thermodynamic solutions providing a chi value of zero or less. Further, the present invention describes solvents for equilibrium thermodynamic solutions having substantially higher dispersion limits than previously believed possible.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What is claimed is:

1. A method of manufacturing an electrode consisting of the steps of:
    a) introducing a group of titanium dioxide nanowires into a solvent to dissolve the group of titanium dioxide nanowires and form a solution consisting of dissolved group of titanium nanowires in the solvent, the solvent characterized by a value of chi less than about 0.01;
    b) applying the solution consisting of the solvent and dissolved group of titanium dioxide nanowires to a surface to produce an assemblage of titanium dioxide nanowires interconnecting electrically in a discrete layer; and
    c) removing the solvent.
2. An electrode consisting of:
    a) an assemblage of titanium dioxide nanowires interconnecting electrically in a discrete layer;
    b) a surface receiving the assemblage of titanium dioxide nanowires; and
    c) a trace amount of a solvent, wherein the solvent is selected from the group consisting of: DMF (N,N-Dimethylformamide), CPO (cyclopentanone), CHP (1-cyclohexyl, 2-pyrrolidine), NMP (N-methyl 2-pyrrolidone), and mixtures thereof.

* * * * *